United States Patent [19]

Keyes et al.

[11] 4,200,238
[45] Apr. 29, 1980

[54] METHOD OF PREPARING A RAPIDLY SOLUBLE AND MACHINE HANDLEABLE PARTICULATE COMPOSITE AND PRODUCT

[75] Inventors: Melvin H. Keyes, Sylvania; Garry L. Moore, Swanton, both of Ohio

[73] Assignee: Owens-Illinois, Inc., Toledo, Ohio

[21] Appl. No.: 921,300

[22] Filed: Jul. 3, 1978

Related U.S. Application Data

[63] Continuation-in-part of Ser. No. 839,160, Oct. 3, 1977, abandoned.

[51] Int. Cl.² .............................................. B02C 17/00
[52] U.S. Cl. ........................................ 241/21; 241/24; 241/27; 241/29; 252/180; 562/566
[58] Field of Search ...................... 241/21, 24, 27, 29, 241/30; 71/DIG. 2, DIG. 1; 210/58; 252/180; 424/361; 562/565, 566

[56] References Cited

U.S. PATENT DOCUMENTS

| | | | |
|---|---|---|---|
| 2,558,923 | 7/1951 | Bersworth | 562/565 |
| 2,845,457 | 7/1958 | Kroll et al. | 562/566 |
| 2,859,104 | 11/1958 | Kroll | 71/1 |
| 3,321,521 | 5/1967 | Kerr | 562/566 X |
| 3,393,233 | 7/1968 | Richter | 562/566 |
| 3,449,414 | 6/1969 | Boettger | 562/566 |
| 3,507,892 | 4/1970 | Bersworth | 562/565 X |
| 3,607,931 | 9/1971 | Hegarty et al. | 562/566 |
| 3,833,590 | 9/1974 | Dazzi | 71/1 |
| 4,036,990 | 7/1977 | Nakai et al. | 424/361 |

*Primary Examiner*—Mark Rosenbaum
*Attorney, Agent, or Firm*—John R. Nelson; David H. Wilson; Myron E. Click

[57] ABSTRACT

A method of economically producing a relatively rapidly soluble machine handleable particulate composite material from a material of relatively low solubility comprising pulverizing a material of low solubility, selecting a first appropriate size fraction from the pulverized material and mixing the selected fraction with a predetermined proportion of water to obtain a composite. The composite is dried at a predetermined temperature for a specified time. The dried composite is pulverized and a second selected appropriate size fraction is obtained. The second size fraction possesses increased solution solubility and machine handleability properties over the starting relatively low solubility material.

22 Claims, No Drawings

METHOD OF PREPARING A RAPIDLY SOLUBLE AND MACHINE HANDLEABLE PARTICULATE COMPOSITE AND PRODUCT

CROSS-REFERENCE TO RELATED APPLICATIONS

This application is a continuation-in-part of U.S. patent application Ser. No. 839,160 now abandoned, filed Oct. 3, 1977 in the name of the inventor hereof and entitled "EDTA Composite".

BACKGROUND OF THE INVENTION

1. Field of the Invention

This invention relates to a method of producing relatively rapidly soluble composite materials which are formed from materials of relatively low solubility and which possess increased machine handleability properties over the starting relatively low solubility material. The method is useful in producing rapidly soluble composites from a wide variety of starting materials. More particularly, the method is particularly suitable for producing rapidly soluble, machine handleable composites of materials which are of clinical importance, such as chelating agents. The method is particularly important in the clinical field since the rapidity with which chelating agents go into solution can determine their relative effectiveness in each application. Many commercially available organic compounds, particularly many chelation agents, are generally not rapidly soluble in solutions, in particular aqueous solutions, and are not readily processed, packaged, and handled by machine. The present invention was developed to overcome these problems.

2. Description of the Prior Art

Most of the known prior art relating generally to rapidly soluble compounds and to chelation compounds involves the synthesis of EDTA, its salts and derivatives, and also to methods of increasing the solubility of various pharmaceuticals. For example, U.S. Pat. No. 2,558,923 discloses a method for treating an aqueous solution which contains a sodium salt of EDTA (ethylenediaminetetraacetic acid) for the purpose of recovering the EDTA from the reaction mixture. The disclosure is primarily directed towards the synthesis and recovery of the diacid for the purpose of using it as an intermediate reaction product in the synthesis of other amino compounds.

Similarly, U.S. Pat. No. 2,845,457 discloses a method of manufacture of EDTA derivatives by using a single-stream, acid-stabilized, equimolar mixture of hydrogen cyanide and formaldehyde, with the reagents being added simultaneously. The method is directed towards the single-step production of EDTA derivatives.

U.S. Pat. No. 2,859,104 discloses a method of using an EDTA derivative, namely, N,N-dihydroxyethyl N',N' dicarboxymethyl ethylenediamine and its salts as an agent to collect, hold, and provide a source of trace metals in plants. The complex of the diamine and a metal is poured near, sprayed on or mixed with the soil of an agricultural product deficient in the metal of interest.

U.S. Pat. Nos. 3,393,233 and 3,449,414 show, respectively, methods for isolating EDTA from copper containing solutions and for the rapid synthesis of EDTA and derivatives by the use of a cascade-reactor system.

U.S. Pat. No. 3,607,931 discloses a method of producing a rapidly dissolving EDTA salt, i.e. the disodium salt wherein a mixed solution of EDTA partial salts is adjusted to a given temperature and a precise pH, to precipitate a very pure, rapidly soluble disodium EDTA. This method involves a somewhat involved procedure and requires a number of reagents for the completion of the reaction.

U.S. Pat. No. 4,036,990 discloses a method to increase the rate of solubility of materials by mixing the materials with a beta-1, 4 glucan, then pulverizing the mixture. This method requires the introduction of a second substance, i.e. the glucan, into the system in which the compound of interest is dissolved. This is undesirable in many areas of clinical and medicinal chemistry.

SUMMARY OF THE INVENTION

An object of the present invention is to form a rapidly soluble composite from a material of relatively low solubility.

Another object of the present invention is to form a machine handleable composite which is capable of being poured, loaded, and transported by machine means without frequent clogging of flow paths.

A further object of the present invention is to form a composite from a material of low solubility with the above characteristics which may be economically manufactured and readily formed from starting materials with a minimum of required steps.

A still further object of the present invention is to produce a rapidly soluble, machine handleable composite material without adding additional contaminating materials to the composite, such as organic binders, dissolving agents, or inorganic compounds.

An object of the invention is to form a rapidly water soluble, machine handleable EDTA composite which is capable of being poured, loaded, and transported by machine means without frequent clogging of flow paths.

A further object of the invention is to form an EDTA composite with rapid water solubility at a low unit cost, and formed in a minimum of steps, using only water and an EDTA to form the composite.

The method according to the present invention produces a rapidly soluble machine handleable composite which is particularly well-suited to dissolving rapidly in aqueous solution, and which is machine handleable. In regard to the machine handleability of the composite, in many cases the materials to be packaged, machine loaded or the like are in powder form. The powders can possibly clog or foul the workings of automated processing machines due primarily to their extremely small size. The composite of the present invention remains in a particulate state during the machine processing steps and does not fragment into a powder, unless subjected to severe vibration or the like. If the composite fragments from its particulate state to the powder state, the powder can clog processing machines and lower production efficiency. The composite of the present invention is produced by reducing the particle size of the material of low solubility to a relatively small particle size by appropriate grinding or milling operations. The material is segregated into selected size fractions. An appropriate size fraction of the material is isolated and mixed with water in a definite predetermined proportion to form a low solubility composite wherein the low solubility characteristics of the material have been altered. The composite is dried under controlled conditions, pulverized, and a second selected size fraction is segregated. This resultant second selected size fraction of the composite material possesses excellent machine manipulation and handling characteristics and is soluble in various solutions, particularly aqueous solutions, at a rapid rate, as compared to the rate of solubility of the starting material.

DETAILED DESCRIPTION OF THE INVENTION

The present invention relates to materials of relatively low solubility. The invention deals more particularly with increasing the rate of solubility of relatively low solubility materials in aqueous solutions. The method according to the present invention produces a composite product which is not only substantially more rapidly water soluble in aqueous solution than the starting material, but one which is also machine handleable, a property which is important in industrial applications of materials particularly organic wherein the materials are processed primarily by machine means. The present invention has been found to be particularly useful for chelating agents.

While the method is applicable generally to organic materials, its application herein is limited to chelating agents, while being aware that the general steps and procedures of the invention are similarly useful for various other organic compounds. Many chelating agents are used in a variety of chemical procedures, in particular chelating agents such as EDTA and its derivatives (ethylenediaminetetraacetic acid), lithium oxalate and many similarly useful chelating agents. These agents coordinate strongly to a wide variety of metal ions, for example the ions of calcium, iron, magnesium and similar ions, to form relatively stable chelates. Chelating agents are generally commercially available in a number of forms, usually as the partial salts such as the EDTA family. Some are available in the acid form of the chelating agent, while still others are available as inorganic salts of the acid chelating agents. Many chelating agents, particularly EDTA and lithium oxalate, form relatively stable compounds with a variety of metal ions. Such chelating agents are used to entrap metals and thereby deactivate them in a number of chemical procedures. Chelating agents, for example, have been used widely to stop catalytic reactions brought about by metal ions. Many chelating agents have also been used in such practical applications as water softening, detergent compositions, electroplating applications, preparations for rust and scale removal, decontamination of radioactive waste, and many clinical applications such as the prevention of blood coagulation, and in many metal ion catalyzed reaction quenching procedures.

Many compounds which are useful as chelating agents are particularly relatively slow to dissolve in aqueous solution, e.g. the EDTA family, with the most notable exception being tetrasodium EDTA, which is usually rapidly water soluble. Unfortunately, the tetrasodium salt of EDTA is known to materially alter the pH of solutions in which it is dissolved. This pH modification property causes the tetrasodium salt to have limited utility as a chelating agent.

Because many chelating agents are slow to dissolve in aqueous solution and because their powdered and crystalline forms are usually difficult to process by machine, these properties have caused them to be extremely expensive for use in certain situations. Additionally, the fact that many chelating agents will not rapidly dissolve in aqueous solution has made them totally unacceptable in certain quenching agent applications where a catalytic reaction must be stopped with some precision by a chelating agent. This must be achieved for the process to become commercially useful.

Since EDTA and lithium oxalate are very useful in clinical procedures they will be discussed in detail, hereinafter. The present method, however, is applicable to a wide variety of compounds which are of low solubility in various solvents. Similarly, while the examples are directed toward the formation of a composite material from a material of relatively low solubility using only one compound, for example, EDTA or lithium oxalate, the method is also applicable to cases where it is desirable to make a chelating agent mixture formed of more than one chelating agent, for example, a mixture of 50% —50% by weight of disodium EDTA and lithium oxalate or a mixture of 50% —50% by weight of EDTA and disodium EDTA. A chelation mixture could be formed by making the rapidly soluble EDTA composite, separately making the rapidly soluble lithium oxalate composite and then mixing the composites together in the correct proportions.

While the rapid solubility properties of the composite material are very important with respect to the material preuse properties such as machine handleability are also important. In many situations where mass use of materials is important, for example loading large numbers of test tubes for clinical use, the machine handleability of the material is also very important. If a material is rapidly soluble once loaded into the test tube, but is very difficult to efficiently load into the test tube it may not be commercially useful. For example, in processing plants where hundreds of test tubes are loaded per hour, if the material is not easily handleable by machine, there will be constant interruptions in the loading process and the economics of the material will be substantially lessened.

To exemplify how a material of low solubility, in this case disodium EDTA, can be processed by the method of the present invention into a rapidly soluble, machine handleable composite, the following general procedure is used. In using disodium EDTA, which has good chelating characteristics and is particularly preferred for clinical use, the following procedure can be followed. The powdered or crystalline starting material of the salt is pulverized into a particulate size by crushing, grinding, or milling. The material can be pulverized using a blade grinder, such as a CRC Micro-Mill, and by conventional ball milling with as many as fifty crushing balls per mill per run.

When using a ball mill with disodium EDTA, for example, it has been noted experimentally that, under some circumstances and sample sources, the salt is pulverized into small particles by crushing up to a certain crushing stage. After passing a certain stage of crushing, large useless particles begin to develop in the pulverized mixture. These large particles may account for as much as 10% by volume of the freshly milled mixture unless avoided. Large particle formation can be avoided, as well as the concomitant recycling of the large particle fraction eliminated, if the milling time is standardized to the particular properties and characteristics of the starting material. This will be a function of the physical nature, i.e. crystalline or powdered, of the starting material as well as the source of supply.

The pulverized salt is then segregated by size fractionation and the most useful in accordance with this invention fraction is retained for further processing. The remaining material which is not selected in the first selection step is repulverized for later use. The size fraction which is used in the case of disodium EDTA is that fraction which passes through a 140 mesh United States standard sieve. The larger particles which do not pass through the sieve may be recycled to be repulverized.

The first selected size fraction is mixed with a definite proportion of water. The proportion of water mixed with the salt is very important and varies substantially and in accordance with the particular starting material or organic compound being used as well as with the particle size distribution within a selected size fraction. Therefore, while the percent of water in the composite varies from composite to composite, the basic method is the same. The fact that the method possesses the flexibility to apply to a large number of starting materials by only determining the optimum amount of water required for each starting material is a very important feature of the invention. For example, when using the disodium salt of EDTA a weight percent of 82%–83% salt and the balance water was found to be the optimum percentage fractions. Accordingly, if 82% salt of EDTA is used, 18% water is added; similarly if 83% salt is used, only 17% water is added. Although there can be a small variation from the optimum percentage mixture for each particular organic compound, the efficiency and usefulness of the composite in accordance with the invention falls off rapidly from the optimum values. After the water is added to the size fraction of the material of low solubility, the resultant composite is thoroughly mixed. At this point, the composite is generally in the form of a semi-solid state and appearance, but will substantially retain its form when removed from a pour mold after about a minute. The semi-solid composite is poured into a suitable mold, usually about one-half inch thick, and allowed to dry.

In the case of the disodium EDTA composite, it has been found that for maximum stability of the composite, air drying is preferred. When the composite is completely dry, it is again pulverized and a second selected size fraction is obtained. It has been observed that for obtaining the maximum usefulness of the composite for mechanical handling and loading a −30 to +60 mesh size is preferred. As used herein the − to + designation means that the sample is introduced into a set of sieves and separated. The fraction which passes the sieve on top, which has the larger diameter holes and thus the lower sieve number, is collected onto a lower second sieve and separated. The material which remains on the second sieve and will not pass through its smaller holes is the size fraction which is desired. As seen above, then, a −30 to +60 mesh sieve fraction are those particles which pass through the 30 mesh sieve, but will not pass through a 60 mesh sieve.

It has been observed that the selected first and second size fractions for each different starting material are not always the same. To determine which size fractions are of the optimum size, a number of first size fractions are selected for a given starting material. This array of first size fractions are mixed with the water in varying proportions and pulverized to yield a second selected size fractions array, all of which are tested for their solubility properties. Thus, in the preliminary stages of the process, the first pulverizing step generates a number of size fractions. Each size fraction is divided and each subfraction is mixed with a different proportion of water. This array of composites is dried, pulverized and separated into different size fractions, each of which is tested for solubility properties. This procedure has shown that the method is variable enough to be used with a wide variety of starting materials, since a great number of possible proportions and size fractions can be tested to give the most rapidly soluble composite composition.

The method economically produces a rapidly water soluble, machine handleable material composite which uses relatively few steps, all of which are conventionally used in laboratory procedures. The method does not require the addition of undesired organic or inorganic substances, which could contaminate the sample into which the composite is dissolved. The only additional substance added is water.

As indicated above, the selected starting material may be crystalline or powdered, depending upon the source of the material. As stated above, after a certain period of time some compounds which are being pulverized by ball milling, for example disodium EDTA, begin to develop larger particles which are useless in this method. Therefore, the period of time which each compound is to be milled or otherwise pulverized must be standardized because the over-all efficiency of the procedure is a function of the total material which can be processed through the procedures of the invention, without recycling a substantial amount of the material. Also, it has been found experimentally that for consistently good results, that after the pulverizing of the starting material and the mixing of the predetermined portion of water, a sheet of the material in a state of semi-solid form of about one-half inch thick dries rapidly and is easily handleable for further processing. In the case of the disodium EDTA/water composite, if the weight ratio varies materially from the 82%–83%/17–18% proportion, the resulting composite is much less useful than the preferred composite. If not enough water is added, all the EDTA is not "wetted" and the composite is unformable and unsatisfactory for use. Conversely, if too much water is added, the composite will not dry properly at the predetermined temperature and, therefore, is not processable into a second selected size fraction. A too wet composite will not form particles, upon repulverizing, which can be easily handleable by machine.

The water used in the preparation of the composite according to the present invention is preferably distilled or deionized water. Such water is used to minimize the free ions which are added to the composite. In many applications free ions will contaminate not only the composite but the sample into which it is dissolved. However, for some applications, a purified water is not necessary, although it is generally preferred according to the present invention. If water is used which contains ions or other contaminants which will react with the low solubility material which is being used to form the composite, the resultant composite, even if it maintains its favorable solubility characteristics, will have reduced effectiveness in its intended use and will adversely affect the commercial usefulness of the composite.

The following Examples set forth specific embodiments of the invention and are used herein to illustrate the usefulness of the present invention. It is provided out that the size fractions selected for a given starting material can vary widely and are a function of the starting material.

EXAMPLE 1

Commercially available crystalline or powdered disodium EDTA (Reagent Grade) is ground to obtain particles passing through a U.S. standard sieve mesh 140. The salt particles are ground in a blade grinder. The +140 mesh particles are retained and recycled while the collected smaller particles are mixed with distilled, deionized water in the proportions of about 17–18% water to about 82–83% disodium EDTA. The newly formed composite is in a semi-solid state and is poured into a mold so that it forms a layer about one-half inch deep. The composite is air dried for a period of time until it is thoroughly dry, and the composite is pulverized in a blade grinder. The particulate produced is sieved and retained between 20 and 140 mesh screens to produce the final composite.

The composite is tested for its solubility in water by adding 10 mg of the composite to 10 ml of distilled, deionized water, and shaken gently. The composite completely dissolved in less than about 0.32 minutes.

EXAMPLE 2

Commercially available crystalline or powdered disodium EDTA is pulverized in a ball mill (CRC Micro-Mill, with 50 crushing balls) to obtain particles passing through a U.S. standard sieve mesh 140. The salt is separated with the large particles reprocessed.

The resultant pulverized material is mixed with distilled, deionized water in the proportions of about 17–18% water to about 82–83% disodium EDTA. The composite formed is poured into a layer about one-half inch deep in its semi-solid form.

When thoroughly dry, the composite is repulverized in a micro-mill and sieved to obtain particles in the size range of −30 to +60 mesh. This size fraction dissolves rapidly in water and is readily handleable by mechanical processing devices.

EXAMPLE 3

Commercially available powdered lithium oxalate (Reagent Grade) is ground to obtain a particle size which passes through a U.S. standard sieve mesh 140. At times, lithium oxalate as obtained from the manufacturer is of such a size, fraction and particulate nature that it need not be ground before sieving through the 140 mesh sieve. The oxalate which has been sieved through the 140 mesh sieve is collected and 355 grams of the oxalate is mixed with 220 milliliters of the distilled deionized water, this is a proportion of 62% by weight lithium oxalate to 38% by weight water. The newly formed composite is in a semi-solid state and is poured from the mortar and pestle in which it is mixed onto a Plexiglas sheet so that the resultant composite is about one-half inch thick over its entire area. The composite is air dried at room temperature for a period until it appears thoroughly dry. The composite is then pulverized in a mortar and pestle with gentle crushing by the pestle. The particulate composite product thus produced is sieved through a −50 to +140 sieve set and the fraction between the sieves is collected.

EXAMPLE 4

Commercially available powdered lithium oxalate is passed through a 140 mesh sieve. The oxalate passing through the sieve is collected and 154 grams of the oxalate is mixed with 83 milliliters of distilled deionized water to form a semi-solid material. The semi-solid material is poured into a suitably sized mold so that the thickness of the resultant semi-solid material within the mold is approximately one-half inch thick over its entire surface. This composite material comprises approximately 65% lithium oxalate by weight and approximately 35% by weight water. The newly formed composite is allowed to air dry at room temperature until it is thoroughly dry. The composite is then gently pulverized using a mortar and pestle and the resultant material is passed through a set of sieves which are −50+140 mesh in nature.

The composite thus produced is tested for solubility in water by adding approximately 15 milligrams of the particulate composite to 10 milliliters of distilled deionized water. The composite completely dissolves in less than twenty seconds with shaking when tested in this manner. Thus, the initial particulate composite is rapidly soluble in water while showing good machine handleability characteristics, in its particulate form just as do the composites of Examples 1, 2 and 3.

We claim:

1. A method of increasing the rate of solubility and machine handleability of a material having a relatively low solubility comprising the following steps:
    a. pulverizing a relatively low solubility material and obtaining a selected first size fraction from said pulverized material,
    b. mixing said first size fraction with a predetermined proportion of water to form a composite,
    c. drying and pulverizing said composite,
    d. obtaining from said pulverized composite a second selected size fraction having an increased rate of solubility and machine handleability.

2. A method of increasing the rate of solubility in aqueous solution and machine handleability of a chelating agent having a relatively low water solubility comprising:
    a. pulverizing a chelating agent and obtaining a selected first size fraction from said pulverized agent,
    b. mixing said first size fraction with a predetermined proportion of water to form a composite,
    c. drying and pulverizing said composite,
    d. obtaining from said pulverized composite a second selected size fraction having an increased rate of water solubility and machine handleability.

3. The method of claim 2 wherein said chelating agent is monosodium ethylenediaminetetraacetic acid.

4. The method of claim 2 wherein said chelating agent is disodium ethylenediaminetetraacetic acid.

5. The method of claim 2 wherein said chelating agent is trisodium ethylenediaminetetraacetic acid.

6. The method of claim 2 wherein said chelating agent is tetrasodium ethylenediaminetetraacetic acid.

7. The method of claim 2 wherein said chelating agent is lithium oxalate.

8. The method of claim 4 wherein said first size fraction is that chelating agent which passes through a 140 mesh sieve.

9. The method of claim 4 wherein said predetermined proportion of water is about 17–18% by weight.

10. The method of claim 4 wherein said second fraction is one which passes through a 20 mesh sieve but will not pass through a 40 mesh sieve.

11. The method of claim 4 wherein said second fraction is one which passes through a 30 mesh sieve but will not pass through a 60 mesh sieve.

12. The method of claim 7 wherein said first fraction is one which passes through a 140 mesh sieve.

13. The method of claim 7 wherein said predetermined proportion of water is about 35–45% by weight.

14. The method of claim 7 wherein said second fraction is one which passes through a 50 mesh sieve but will not pass through a 140 mesh sieve.

15. A particulate composite fraction which is rapidly soluble and machine handleable, said composite being initially a material having normally a relatively low solubility, said composite obtained from a selected first sized fraction of pulverized said low solubility material which first fraction is mixed with a predetermined proportion of water, dried and again pulverized and then again selectively sized to obtain said particulate composite fraction.

16. A particulate composite fraction which is rapidly water soluble and machine handleable, said composite being initially a chelating agent having normally a relatively low solubility, said composite obtained from a selected first sized fraction of pulverized said low solubility chelating agent which is mixed with a predetermined proportion of water, dried and again pulverized, and then again selectively sized to obtain a particulate composite fraction.

17. The composite of claim 16 wherein said chelating agent comprises ethylenediaminetetraacetic acid.

18. The composite of claim 16 wherein said chelating agent is monosodium ethylenediaminetetraacetic acid.

19. The composite of claim 16 wherein said chelating agent comprises disodium ethylenediaminetetraacetic acid.

20. The composite of claim 16 wherein said chelating agent comprises trisodium ethylenediaminetetraacetic acid.

21. The composite of claim 16 wherein said chelating agent comprises tetrasodium ethylenediaminetetraacetic acid.

22. The composite of claim 16 wherein said chelating agent comprises lithium oxalate.

* * * * *